United States Patent [19]

Rogers, III et al.

[11] Patent Number: 5,617,671
[45] Date of Patent: Apr. 8, 1997

[54] METHOD FOR GROWING TURFGRASS INDOORS UNDER REDUCED LIGHT CONDITIONS

[75] Inventors: John N. Rogers, III, Haslett; John C. Stier, Lansing; Paul E. Rieke, Okemos; James R. Crum, Williamston, all of Mich.

[73] Assignee: Board of Trustees operating Michigan State University, East Lansing, Mich.

[21] Appl. No.: 258,584

[22] Filed: Jun. 10, 1994

[51] Int. Cl.$^6$ ........................................ A01G 9/02
[52] U.S. Cl. ........................................ 47/58
[58] Field of Search ........................................ 47/58

[56] References Cited

U.S. PATENT DOCUMENTS

| | | | |
|---|---|---|---|
| 4,704,160 | 11/1987 | McVey | 71/92 |
| 4,802,314 | 2/1989 | Schildge | 52/6 |
| 5,010,695 | 4/1991 | Schildge | 52/6 |
| 5,103,600 | 4/1992 | Geiger | 52/6 |
| 5,187,894 | 2/1993 | Ripley | 47/86 |

FOREIGN PATENT DOCUMENTS

| | | | |
|---|---|---|---|
| 3219804 | 3/1991 | Japan | 47/86 |
| WO92/05690 | 4/1992 | WIPO | 52/6 |

OTHER PUBLICATIONS

Ferguson, M. H., (ed.), et al. "Air Circulation" *Building Golf Holes for Good Turf Management* 1968, U.S.G.A. p. 34.

Musser, H.B., "Soil and Turf Relationships"; Drainage and Irrigation; Turf Maintenance; and, Turf Diseases and Similar Types of Injury *Turf Management* 1962 McGraw–Hill Book Co., N.Y. pp. 12–17, 62–65, 173, 218–219, and 238–239.

Primary Examiner—James R. Feyrer
Attorney, Agent, or Firm—Ian C. McLeod

[57] ABSTRACT

A method for growing turfgrass indoors on an activity field under reduced light conditions, The method uses a Type II plant growth regulator (PGR) and particular conditions for growth, The result is a high quality activity field of turfgrass capable of withstanding traffic from multiple athletic events.

12 Claims, 1 Drawing Sheet

METHOD FOR GROWING TURFGRASS INDOORS UNDER REDUCED LIGHT CONDITIONS

BACKGROUND OF THE INVENTION

1. Field of the Invention

The present invention relates to a method for growing turfgrass indoors on an activity field under reduced light conditions. In particular, the present invention relates to a method wherein permanent indoor grass or removable modules are used to provide the activity field.

2. Description of Related Art

The prior art has attempted to grow turfgrass indoors under reduced light conditions. The result has been to produce turfgrass which dies rapidly and/or is sparse and disease ridden. Various mechanical means for providing turfgrass indoors are disclosed in WO92/05690 and U.S. Pat. No. 5,187,894 to Ripley and U.S. Pat. No. 5,010,695 to Schildge; U.S. Pat. No. 4,802,314 to Schildge; and U.S. Pat. No. 5,103,600 to Geiger. Japanese Patent Application 3,219,804 describes the use of plant growth regulators with seeds. Such alternatives are very expensive and/or have limited effectiveness.

OBJECTS

It is therefore an object of the present invention to provide a method for growing and maintaining turfgrass indoors. Further, it is an object of the present invention to provide a method which is reliable and economic. These and other objects will become increasingly apparent by reference to the following description and the drawings.

DESCRIPTION OF PREFERRED EMBODIMENTS

Figure 1:
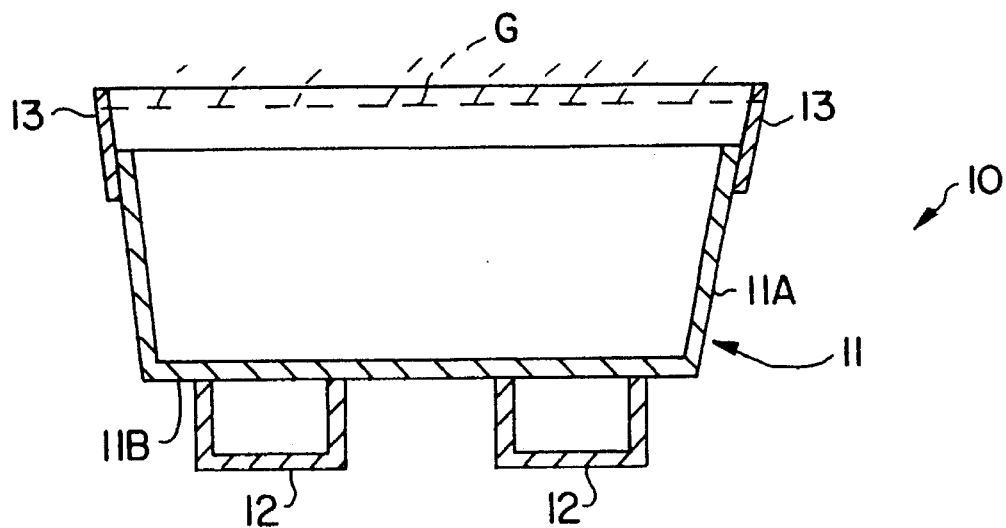
FIG. 1 is a front cross-sectional view along line 1—1 of FIG. 2 of an individual modular container 10 used to grow the turfgrass G.

The present invention relates to a method for providing an indoor activity field with natural turfgrass under reduced light conditions which limit growth of the turfgrass which comprises: periodically applying a Type II plant growth regulator (PGR) to the turfgrass which inhibits gibberellin biosynthesis while maintaining low surface moisture and providing air movement over the turfgrass and while using disease control chemicals and fertilizing chemicals, including nitrogen, potassium, phosphorus, iron and magnesium, with a radiation level of at least about 1 mol/day PAR (Photosynthetically Active Radiation) on the indoor activity field. The amount of above-ground biomass production of the turfgrass is reduced with the chemicals to promote greater quality under the reduced light conditions.

Further, the present invention relates to a method for providing an indoor activity field with natural turfgrass under reduced light conditions which limit growth of the turfgrass which comprises: providing the turfgrass in multiple assembled containers each liftable and moveable with a fork type lift truck and containing a soil which is substantially sand so that the soil resists compaction, in an outdoor setting which is exposed to ambient light adjacent to the activity field and with cutting and watering as needed; applying a Type II plant growth regulator (PGR) which inhibits gibberellin biosynthesis to the turfgrass just prior to moving the containers with the forklift truck to the indoor activity field; fitting the modular containers together on a flat base defining the indoor activity field; using the indoor activity field for an activity for a period of time between about 10 and 60 days, while maintaining low surface moisture, providing air movement (circulation) over the turfgrass, increases and using disease control chemicals and fertilizing chemicals including nitrogen, potassium, phosphorus, iron and magnesium and with a radiation level of at least about 1 mol/day PAR on the indoor activity field; and removing the modular containers to the outdoor setting for a period of time to rejuvenate the turfgrass for subsequent use on the indoor activity field.

A functional athletic field must have a smooth, turf-covered, and relatively divot free surface. It must be well drained, both internally and from a surface standpoint so that water is used only to support plant life. The turfgrass chosen must be adapted climatically, and must be wear tolerant and/or able to recuperate following normal, but not too excessive use. The ability of a plant to recover from traffic is critical. Further, the proper conditions for growth are essential for the turfgrass system to thrive. These conditions include proper soil type, fertility, pest control, water, and light. Light is critical to the plant as it utilizes light energy through photosynthesis to convert elements to starches and sugars usable by the plant. Without adequate light the turfgrass plant, even in a nontrafficked situation, will eventually die. Turfgrass death is greatly accelerated in a sports field situation. Inadequate light for turfgrass growth and recovery is the primary reason for the lack of use of natural turfgrass as a permanent surface in domed stadia.

The present invention provides the parameters necessary for maintaining turfgrass for sports fields in domed stadia and other reduced light situations (RLC) on a long term (2 to 12 months) or permanent basis where there is no turfgrass replacement. The most economical means was identified for maintaining turfgrass under reduced light conditions, first by identifying the minimum amount of light necessary to maintain sports turf. Also important were the use of fertilizers, growth regulators, pesticides, and water in very specific amounts at critical periods such that the growth and recuperative ability of the grass matched the light energy levels received by the plant. A management plan is disclosed in a very specific recipe form for maintaining turfgrass under reduced conditions. The stadium owner/manager has the option of having natural grass on a long term basis, without the cost of repeated installations which are necessary under traditional management programs.

The unique inputs for management of a sports field or turf area in a reduced lighting situation are described in the following paragraphs.

SOIL DESCRIPTION

Figure 2:
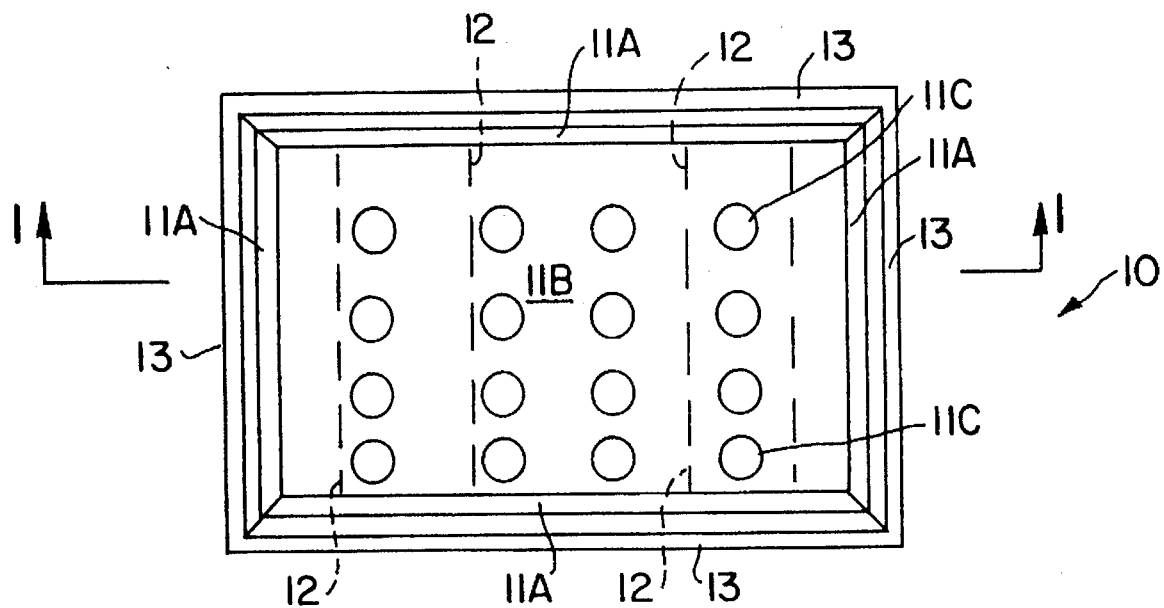
FIG. 2 is a plan view of the modular container 10 shown in FIG. 1.

FIGS. 1 and 2 show an individual module 10 to be used in the present invention for covering an activity field. A lower box-shaped portion 11 has four (4) upwardly extending sides 11A which are inclined slightly (about one (1) degree) outward and a bottom 11B. The bottom 11B supports forklift tubes 12 which allow the module 10 to be moved indoors and outdoors. Around the top of the sidewalls 11A is a rectangularly shaped retainer 13 which is removable after the module 10 with the soil and grass is moved into position adjacent other modules 10 inside a stadium or the like. The ground level G is adjacent the uppermost portion of the retainer 13, as shown by the dotted lines. The bottom 11B has perforations 11C which allow water drainage. The modules 10 contain between about 50 to 100 square feet of surface area at the ground G level and are preferably made of lightweight metal. The holes 11C are preferably about 1⅜" in diameter. The sides 11A are preferably about 3" high and the retainer is about 3" high. The tubes 12 are preferably about 3" high. The sides 11A are tapered outward to insure a close fit of the turfgrass in the modules 10 when they are fitted together.

The preferred soil used for the transportable sports field consisted of a mixture of 80% sand that has a particle-size distribution closely following United States Golf Association (USGA) specifications for root zone mixtures (no more than 10% of the weight being between 1.0 and 3.4 mm (very coarse sand and fine gravel) with a maximum of 3%>2 mm;>60% between 0.25 and 1.0 mm (coarse and medium sand); up to 20% between 0.15 and 0.25 mm (fine sand); no more than 5% between 0.05 and 0.15 mm (very fine sand); no more than 5% between 0.002 and 0.05 mm (silt) and; no more than 3% less than 0.002 mm (clay)), 10% organic soil (sapric peat), and 10% native sandy loam textured (about 70% sand, 20% silt, and 10% clay) A horizon (topsoil). This mixture is used for the reason that after attaining maximum compaction, aeration porosity remains great enough to allow for an infiltration rate and hydraulic conductivity (Ksat) of water at greater than four (4) inches per hour. The addition of the organic soil (sapric peat) increases the ability of the soil to hold plant-available water against the pull of gravity and increases the cation exchange capacity (CEC) of the soil so that nutrients important for plant growth are held in the soil. The native sandy loam textured A horizon adds a small amount of organic matter (indigenous to topsoil) and slightly increases the silt and clay contents of the final soil mixture. The resultant mixture contains approximately 88% sand, 6% silt, and 6% clay with approximately 2% organic matter content (all by weight).

The sand used in the soil mixture is subrounded to angular in shape to allow the soil to stabilize and attain maximum compaction so little soil movement occurs upon loading by machinery or players. The sands included in the soil mixture are calcareous (contain free calcium carbonate) and the soil mixture pH is approximately 8.0. Inherent macronutrient (nitrogen, phosphorous, and potassium) contents are managed by fertilizer addition since all values will be low as measured by soil testing.

LIGHT

Light is generally the limiting factor for turfgrass growth in areas receiving less than one-third full sunlight for at least eight hours of an eight to twelve day length (photoperiod). Turfgrass grown in reduced light conditions is sparse, spindly, and exhibits poor color and quality. Turfgrass grown under RLC has a low tolerance for traffic and poor recuperative abilities. Traditional management practices for turfgrass in full sunlight do not work well for turfgrass in reduced light conditions. The present invention provides unique management practices which allow the maintenance of a high quality turfgrass for both sports and aesthetic purposes under reduced light conditions. One part of this invention has been aimed at defining the levels of light to be considered as reduced and insufficient light for turfgrass growth and management. The definition includes the amount of light needed for both short term and long term (2–12 months) or permanent use of turfgrass in insufficient and reduced light situations.

DEFINITION OF REDUCED LIGHT

Reduced light is the amount of light which is below the level of light required for maximum photosynthesis. This level of light may be well above the compensation point (the point at which photosynthesis exceeds respiration) of the turfgrass and may be of suitable quantity to stimulate normal-appearing turfgrass growth and regeneration. However, under reduced light, turfgrass growth rates, habits, morphology, and/or physiology differ from turfgrass growth under full sunlight conditions (e.g excessive production of gibberellic acid and plant cell elongation under RLC). Certain turfgrass pests and/or diseases may commonly appear under conditions of reduced light which are rare or non-existent under conditions of full sunlight (e.g. powdery mildew (*Erysiphe graminous*) or snow mold diseases (*Typhula* or *microdochium* spp.)). The actual level of light to be considered as reduced light depends on any combination of a number of factors, including, but not limited to, turfgrass species, temperature, plant carbohydrate and nutrition levels, plant and environmental moisture levels, $CO_2$ levels, $O_2$ levels and the like.

On average, any situation in which the turf receives less than one-third full sunlight is considered a reduced light condition. One-third of full sunlight during the summer is approximately 650 $\mu mol/m^2/s$ of PAR (Photosynthetically Active Radiation; i.e. visible light from 400–700 nm). Thus, a reduced light condition is one in which, on average, the quantity of light irradiant upon the turfgrass is less than 650 $\mu mol/m^2/s$ from two hours before and two hours following the daily solar zenith, or less than 20 mol/day PAR over at least an eight hour day/month (photoperiod).

DEFINITION OF INSUFFICIENT LIGHT

Insufficient light is the amount of light which is below the compensation point of the turfgrass. The turfgrass ceases growing and eventually dies under conditions of insufficient light. Although turfgrass can remain alive for an indefinite period under insufficient light, the amount of time and the speed of decline depend largely on the amount of carbohydrate (energy) reserves in the turfgrass plants. The amount of light considered insufficient varies depending on: 1) the type and condition of the turf used 2) the environmental conditions (temperature, $CO_2$, water, and the like). Generally, insufficient light can be considered to be any quantity less than 6 mol/day over an approximate 8 hr photoperiod for cool season grasses. Due to variability among species and cultivars, the quantity and duration of light to be considered insufficient for a warm season grass would be greater than 6 mol/day.

MAINTENANCE OF TURFGRASS UNDER REDUCED LIGHT: SHORT-TERM

The minimum light level for a short-term (4 to 6 weeks) installation and use of a turfgrass surface is 1.0 mol/day of PAR when the other conditions and treatments described herein are applied to the system (notably the use of plant growth regulators and fertilizers). Average daily light levels below 1.0 mol/day PAR result in shorter time periods for maintaining an acceptable turfgrass for sports play.

After an approximately six week period, the turf must be regenerated under a light regime above the compensation point (e.g. moved outdoors to receive full sunlight). For cool season grasses, the photoperiod should last for at least eight hours/day until the turf is sufficiently recovered; for warm season grasses, the photoperiod should be for at least 12 hr/day.

MAINTENANCE OF TURFGRASS UNDER REDUCED LIGHT: LONG-TERM

A long term or permanent installation of a turfgrass surface for sporting events or other high traffic usage must include sufficient lighting to consistently exceed the compensation point, promoting the generation of new tissues and plant parts to replace those destroyed by traffic. A root:shoot ratio of at least 2:1 is desired. The requisite light level depends on many factors as previously described.

The minimum light level for a long-term or permanent installation of a high quality turfgrass system for high traffic usage is between 10–15 mol/day PAR (photosynthetically Active Radiation). The light is fairly evenly distributed over a time period of at least hours; 12–15 hours is preferable. Those light levels can be obtained via artificial sources or through light transmitting covers. Other specific inputs as described herein (particularly plant growth regulators and fertilizers) are required to maintain a high quality turfgrass.

Artificial light (using High Intensity Discharge, or HID, lamps) can be used to achieve the required light level. Many types or combination of light sources can be used, including low/high pressure sodium, metal halide, MHN, microwave, and argon lamps. Generally, fluorescent, incandescent, tungsten, and mercury vapor lamps will not provide sufficient wattage and/or appropriate wavelengths for turfgrass growth.

The light sources must not be used in such a manner that the temperature of the turf is raised to harmful levels. Lamps which transmit a high level of ultraviolet (UV) light or a disproportionate level of red:blue or red:far red light are to be avoided. Lamps which supply a balanced spectrum of PAR are preferred. Low or high pressure sodium, metal halide, MHN, microwave, or argon lamps are examples of suitable lighting sources.

The lamps are sufficiently powerful to transmit an acceptable quantity of PAR to the turf while being distant enough so that the lamps are not physically in the way of any field maintenance practices (mowing, irrigation, etc.). The lamps can be used in conjunction with auxiliary lighting sources for media purposes.

PGRs AND LIGHT

The use of Type II plant growth regulators (PGRs) to inhibit gibberellin biosynthesis for obtaining and maintaining a high quality turf is essential at light levels below 20 mol/day PAR for both short and long term reduced light conditions. The PGRs are applied repetitively at below or labelled rates. PGRs are preferably applied at increasingly longer time intervals until a steady state exists and subsequent applications do not harm the turfgrass, for example: the first two applications can be 6 weeks apart, but the third application can follow 8–10 weeks subsequent to the second application to allow time for potentially toxic effects of the preceding PGR applications to dissipate. Generally, the rates should decrease as light levels decrease from a 15 mol/day standard.

AIR MOVEMENT

Proper air movement is critical for maintenance of turfgrass in reduced lighting situations. Air movement provides $CO_2$ to the plants for photosynthesis. Air movement also enhances the reduced rate of evapotranspiration in reduced light situations, important for maintaining turfgrass plant turgidity. Proper turgidity is necessary to provide for a better quality of cutting and avoid matted turf which traps moisture and serves as suitable environment for turf diseases. Air movement is also important to remove free surface moisture following irrigation or dew and guttation formation which would facilitate several turf diseases. Fans or blowers, placed either above, adjacent to, or on the field, are used when necessary to provide suitable air movement. The desired air movement is 3 to 5 mph. The fans can be portable or fixed. Vacuum or heat mechanisms can also be used to promote drying of the turf surface.

WATER

Water is an absolute necessity for any plant system. Water is used in plants to drive photosynthesis, to transport minerals and metabolites within the plant, and to maintain the structural integrity of the plant's cells and the plant's morphology.

Water is applied to turf under RLC only when necessary to avoid drought stress and as a vehicle to supply fertilizers and chemicals to the turf system. Irrigation to avoid drought stress is generally applied deeply and infrequently as needed to recharge the turf/soil system. Light, frequent applications of water are typically avoided as this enhances disease potential. Watering can be performed either by overhead or subsurface methods. Extended periods of free water on the turfgrass surface or in the thatch/mat layer is avoided as this encourages disease organisms. Excess water can be removed using fans/blowers, squeegees, heat, or vacuum systems.

CHEMICAL AND FERTILITY TREATMENTS UNDER REDUCED LIGHT CONDITIONS

The growth and maintenance of turfgrasses for sports turf under reduced light conditions (RLC) is dramatically influenced by chemical and fertility practices of the turfgrasses. The fertility practices are used for growth and development of the turfgrass. Chemical management of the turf is used for disease management and growth regulation. These practices are certainly co-dependent on each other in all manners of maintaining acceptable grass, as a mispractice in any area causes a certain demise of turf and playing quality of the field.

CHEMICAL MANAGEMENT

DISEASE MANAGEMENT

The first area of chemical management is in the area of turfgrass disease control. When turfgrass is maintained under RLC, it is susceptible to low light diseases such as gray snow mold (*Typhula* spp.), pink snow mold (*Microdochium nivale*), rust (*puccinia* spp), powdery mildew, and leaf spot/melting out (*Dreschlera/Bipolan* spp.). Because of an inherent slow recovery time of grasses that are subjected to these pathogens that are under RLC, it is imperative that the grasses be treated on a preventative basis with contact and systemic fungicides. Examples of suitable contact fungicides include dithiocarbamates (mancozeb), and chlorothalonil. Suitable locally systemic fungicides include dicarboximides (iprodione and vinclozilin), while suitable systemic fungicides include benzimidazoles (e.g. thiophanate-methyl) and ergosterol biosynthesis inhibitors (e.g. fenarimol, propiconazole). Metalaxyl, propamocarb, and fosetyl aluminum fungicides are to be used to control pythium diseases when they occur under RLC. If there is an outbreak of disease under RLC these chemicals effectively stop the pathogens. However, recovery is slow. Systemic fungicides can also be used on a preventative and/or curative basis. Their use is limited due to the potential for resistance of the pathogen(s) to the chemical. These include sterol-biosynthesis inhibitors and benzimidazoles.

Climatic conditions other than light will also affect disease pressure and chemical management. Moisture and humidity levels must be kept at optimum levels. This usually necessitates air movement at 3–5 mph over the entire field surface in order to ensure a proper and timely drying of leaf surfaces after necessary periods of darkness and subsequent exudate formation (guttation water).

GROWTH REGULATION

The plant maximizes $CO_2$ fixation at about one third full sunlight (approximately 20 mols/day PAR, or 650 $\mu$mol/m$^2$/s PAR.) One key element is to determine the energy level below one third full sun where turfgrasses can be maintained for sports turfs. The light level must be sufficient to provide a turfgrass surface both playable and able to recuperate from sports related traffic. However, even after this level is ascertained one cannot assume that the light spectrum necessary for plant growth is in the best ratios for turfs subjected to sports traffic. Plants grown under RLC are spindly and etiolated primarily because of a lack of blue and bluegreen wavelengths (400–500 mm) which promote prostrate growth. Plants growing under RLC receive primarily longer wavelengths of light (orange, red, and far red) which promote cell elongation. In full sun the ratio of blue to red light is greater than 1:1 while in RLC the ratio is $\leq$1:1. The elongated cells are normally thin walled and lead to a weakened plant unable to support traffic and susceptible to invasion by pathogens. To prevent cell elongation, a type II growth regulator must be applied to an actively growing turfgrass species. The plant must be actively growing for chemical uptake and metabolism. A type II growth regulator is one that slows down plant cell elongation or inhibits biosynthesis of gibberellic acid by the plant. This is as opposed to a type I growth regulator which stops plant cell division. Because the type II growth regulator only slows down cell elongation, (not stops) and the plant is still receiving energy through PAR wavelengths in the 600–750 mm range, then the energy can be transferred to prostrate growth, albeit slowly. The important point is that there is still some growth from the energy and it is not in the form of cell elongation.

The type II growth regulators suited for this purpose are paclobutrazol, flurprimidol and trinexapac ethyl. One example is flurprimidol applied to an actively growing plant via label recommendations at a rate of 0.5–1.0 lb ai/acre (active ingredient) at intervals not less than six weeks. The chemical must be thoroughly watered into the ground as it is root absorbed. Rates of product decrease and interval between applications increases as the duration of the field under RLC increases.

FERTILITY

For proper turfgrass growth and development there must be an adequate amount of nutrients that are properly balanced. The majority of the sixteen essential nutrients for turfgrass growth are usually present in adequate amounts. There are, however, five elements that must be added to this turfgrass system when under RLC. These elements are nitrogen, potassium, phosphorous, iron, and magnesium. Each can cause a problem if not present in adequate amounts, however, the amount of total nutrient needed varies widely with nitrogen and potassium dominating the list, followed by phosphorous and lastly, iron and magnesium. Levels of these elements in the soil (media) are monitored on a regular basis with corrective applications made in addition to the regular fertilization program when soil or foliar testing indicates corrective applications are necessary. Foliar tests are conducted for adequate fertility levels on an occasional basis.

NITROGEN

The normal practice for turfgrasses grown under RLC is to closely monitor and keep nitrogen levels low as the nitrogen would only promote spindly etiolated growth under these conditions. This provides for an adequate turf under some shaded situations so long as the traffic is minimized. In a sports turf situation there must be a surface capable of withstanding traffic. Since Type II growth regulator is applied to the turfgrass system to slow down cell elongation and promote prostrate growth then additional nitrogen can and must be supplied. The nitrogen promotes lateral or prostrate growth, thereby aiding in recuperation.

It is important that the nitrogen application be at intervals similar to growth regulator applications but the application dates be spaced between the growth regulator application dates. The first nitrogen application is 7–10 days before the first growth regulator application. The nitrogen is in both slow and quick release forms preferably at about a 50/50 ratio. The range is 30 to 70 and 90 to 10 slow to quicker release forms. The amount of nitrogen is between 1.0– 2.0 lbs N/1000 ft$^2$/month, depending on turfgrass species.

POTASSIUM

Potassium is vital for turfgrass growth and development and if limiting can lead to decreased stress tolerance particularly from traffic. A potassium deficient turfgrass system under RLC is compounded by slower turfgrass recovery. Subsequently, a turfgrass system with a soil media with a low cation exchange capacity (CEC) readily leaches potassium through the soil profile and requires constant additions of potassium.

The turfgrass per 1000 square feet system under RLC requires between 1.0–2.0 lbs K$_2$O/1000 ft$^2$/month. The variance on this requirement stems from the CEC of the soil media and subsequent potassium availability to the plant.

PHOSPHOROUS

Phosphorous is important for turfgrass rooting and seedling development. It must be supplied in adequate amounts and is often deficient in sand based root zones. The turfgrass system under RLC requires 0.15–0.30 lb P$_2$O$_5$/1000 ft$^2$/month.

IRON

Iron is used to provide improved turfgrass color without adding nitrogen. It has also been shown to increase chlorophyll content and improve turfgrass quality and wear tolerance under RLC. The turfgrass system under RLC will require 0.1–0.4 lbs Fe/1000 ft$^2$/month.

MAGNESIUM

Additional magnesium applied to a turfgrass system under RLC has shown an increased synthesis of chlorophyll. This is exhibited by a plant that is more stress tolerant and has an overall better turfgrass quality. This magnesium application must be coupled with an iron application for desired results to be achieved. The turfgrass system under RLC requires 0.1–0.4 lbs Mg/1000 ft$^2$/month.

WATER

Water is an absolutely essential input for any plant system. Water is used to drive photosynthesis, to transport minerals and plant products within the plant, and to maintain structure integrity of the cells and the plant. Water is applied to the plant only when necessary to avoid drought stress and to water-in fertilizers and PGRs. Watering-in of fertilizers and PGRs is performed only to such a depth so as to place the PGR's and fertilizers within a position for uptake by the roots (generally ½"). Additional watering is performed deeply and infrequently to avoid drought stress. Light, frequent applications of water is generally avoided as they enhance disease potential and shallow rooting. Watering is performed either by overhead or subsurface methods.

EXAMPLE 1

The following Example describes maintenance practices for a portable turfgrass system which was established under optimal conditions (e.g. outdoors) during all or part of the growing season, then moved into a reduced light situation (e.g. enclosed stadium). The management practices described below were for an established field, at least 12 months old, in a temperate, continental climate (e.g. the state of Michigan in the United States). Lack of sufficient light is the major obstacle to maintenance of the turfgrass in a stadium. It is assumed there was less than 5 mol of photosynthetically active radiation (PAR) per day.

The field was constructed of close-fitting hexagonally and trapezoidally shaped modules filled with soil and turfgrass developed by Three Dimensional Services of Rochester Hills, Mich. for the present application and described in The Detroit Free Press Jun. 17, 1993. The soil was a mixture of sand:peat:soil in an 8:1:1 ratio (v/v) and particle size analysis of approximately 88% sand (2.0–0.05 mm) and maximum of 6% clay particles (<0.002 mm). The turfgrass sward was a mixture of Kentucky bluegrass (*Poa pratensis* L.) and perennial ryegrass (*Lolium perenne*), planted in an 85:15 ratio (w/w). The management of weeds and insects was not described as these are unique to a given situation, and, if the field is properly established and maintained, weed and insect problems can be considered to be negligible.

The following description assumes no weed or insect problems are important. Due to the ubiquitous nature of fungal turfgrass diseases, however, management of the most likely types of turfgrass diseases is described. All weed, insect, and disease management concerns are based on knowledge and experience gained by the authors during the course of conducting 21 experiments, during a 23 month period, in conditions similar to the ones assumed in this description. The knowledge gained included that gained from the construction, installation, and management of a full scale portable, indoor/outdoor soccer field at the Pontiac Silverdome, Pontiac, Mich. The descriptions are also based on knowledge gained during the management of a 320 ft$^2$ simulator turfgrass field permanently housed inside a facsimile of the Pontiac Silverdome stadium on the campus of Michigan State University, East Lansing, Mich.

Description of Management practices for the assumed parameters

In general, the carbohydrate levels and turf density were optimized while the turfgrass is under optimal growing conditions (e.g. full sunlight; outdoors). Adequate fertilization, watering, and frequent mowing (daily) during the growing season were maintained prior to moving the turf indoors.

Ten to 12 days prior to movement of the turfgrass indoors it was very important that a Type II growth regulator (e.g. flurprimidol or trinexapac-ethyl) was applied to the turfgrass. Regular mowing and watering was reinstated at appropriate intervals.

A broad-spectrum fungicide was applied to the turf two to three days prior to movement of the turfgrass indoors. The fungicide must be active against pink snow mold, leafspot/melting out, dollar spot, and rust. A tankmix of two or more fungicides was usually needed. For short-term indoor installations, 1–20 days, a contact fungicide alone was sufficient (e.g. chlorothalonil, iprodione, vinclozolin, pentachloronitrobenzene). For longer short-term installations (>20 days indoors) or long-term installations, a contact fungicide was applied in conjunction with a compatible systemic fungicide (e.g. fenarimol, propiconazole, triadimefon or thiophanate-methyl).

The turfgrass soil system was irrigated to field capacity immediately prior to, or during, movement of the turfgrass indoors. Sufficient natural precipitation at this time may also suffice. This step was necessary to ensure adequate moisture in the soil system to sustain the turfgrass for up to 20–60 days to minimize or preclude the need for (overhead) irrigation once indoors. If the capability of subsurface irrigation exists once the turfgrass is indoors then this step can be omitted. Overhead irrigation when the turf is indoors is undesirable due to the propensity for the development of turfgrass diseases to develop in the free surface moisture resulting from overhead irrigation. If overhead irrigation is necessary then fans or other means must be used to dispel the free surface moisture. Because of a reduced light situation, constant air movement must be present to reduce humidity levels.

Once indoors, the turf was mowed daily. Clippings were removed to guard against them serving as a food source for opportunistic pathogens and to prevent the buildup of unsightly clipping waste. Prior to mowing, the turf was encouraged to stand upright to ensure a proper cut. This was generally performed by brushing the turf before mowing (e.g. pulling a brush behind a utility vehicle) and using groomers on the mowers.

Free surface moisture (dew, guttation fluids) were removed daily to inhibit fungal pathogens. Free moisture was removed prior to mowing. Moisture was dried off the plants so that it vaporized, rather than merely knocking it off the plants by poling or mowing, processes which only place the free moisture directly into the most likely infection courts inhabited by fungal pathogens. Fans can be used to vaporize the free moisture. Alternatively, turf vacuums can be used to remove the moisture from the turf environment.

The following Table 1 shows a timeline for management practices and chemical inputs for a portable turfgrass athletic field from the beginning of the growing season, through a 30 day indoors installation, and subsequent rejuvenation and maintenance outdoors until the onset of winter dormancy.

TABLE 1

| Date | Action |
|---|---|
| April 4 | Apply 1 lb nitrogen per 10 ft$^2$ using a slow release, sulfur coated urea (SCU). All other nitrogen applications are to be fast release N sources unless specifically designated otherwise. |
| April 5 | Apply 2 lb potash per 1000 ft$^2$. |
| April 6 | Irrigate field to solubilize the fertilizer if no precipitation has occurred. |
| April 14 | Apply 1 lb phosphate (P$_2$O$_5$) and 0.5 lb nitrogen, 0.5 lb potash per 1000 ft$^2$. |
| April 15 | Irrigate field if no precipitation has occurred. |
| April 28 | Apply 0.5 lb nitrogen, 1.0 lb potash per 1000 ft$^2$. |
| April 29 | Irrigate field if no precipitation has occurred. |
| May 12 | Apply 0.5 lb nitrogen, 0.25 lb phosphate, and 0.5 lb potash per 1000 ft$^2$. |
| May 13 | Irrigate field if no precipitation has occurred. |
| May 26 | Apply 0.5 lb nitrogen, 0.25 lb phosphate, and 0.5 lb potash per 1000 ft$^2$. |
| May 29 | Apply 1 lb/acre of flurprimidol or 2.25 pts/acre trinexapac-ethyl (plant growth regulator). |
| June 6 | Apply 0.5 lb nitrogen, 0.25 lb phosphate and 0.5 lb potash per 1000 ft$^2$. Irrigate if no precipitation occurs. |
| June 8 | Irrigate sufficiently to fully solubilize the fertilizer if needed. Apply 0.1 lbs Fe and Mg/1000 ft$^2$. |
| June 9 | Apply preventive fungicide mix to prevent pink snow mold (*Microdochium nivale*), leafspot/melting out diseases (*Bipolaris/Drechslera* spp.), etc. |
| June 10 | Move field indoors. |
| June 11 to July 16 | Brush and maintain the field as described above. the field can be rolled when necessary to smooth the playing surface. Visible seams or gaps between modules are to be topdressed with green colored sand or soil. Irrigation is to be performed only when needed, and free surface moisture must be immediately removed. |
| July 17 | Move the field outdoors to rejuvenate the turfgrass. Irrigate. |
| July 19 | Overseed or resod any worn or damaged areas. Apply 1 lb phosphate and 0.5 lb nitrogen, 0.5 lb potash per 1000 ft$^2$. |
| July 20 | Irrigate if necessary to solubilize the fertilizer. |
| July 21 | Maintain frequent (bidaily) mowing. If turf was previously maintained at <2" ht., increase height of cut to 2" for 10 days or until sward has recovered and worn/thin areas have filled. Topdress with the same soil mix used for field construction (minus any peat) at least weekly until worn/depressed areas are levelled. Rolling may be applied in conjunction with topdressing to help level the surface. |
| July 27 | Apply 0.5 lb SCU per 1000 ft$^2$. |
| August 3 | Apply 0.5 lb potash per 1000 ft$^2$. Irrigate if necessary to solubilize the fertilizer. |
| August 31 | Apply 0.5 lb nitrogen, 0.5 lb phosphate, and 0.5 lb potash per 1000 ft$^2$. Irrigate if necessary to solubilize the fertilizer. |
| Sept. 21 | Apply 0.5 lb nitrogen, 0.5 lb phosphate, and 0.5 potash per 1000 ft$^2$. Irrigate if necessary to solubilize the fertilizer. |
| Oct. 10 | Apply 0.5 lb nitrogen, 0.25 lb phosphate, and 0.5 lb potash per 1000 ft$^2$. Irrigate if necessary to solubilize fertilizer. |
| Nov. 20 | (Dormant nitrogen application) Apply 1 lb nitrogen using SCU and 1 lb potash per 1000 ft$^2$. |
| Dec. 10 | Apply a fungicide to prevent pink and gray snow mold diseases (e.g. propiconazole, iprodione, chlorothalonil, anilazine, mancozeb). |
| Dec. 12 | Cover the turf if necessary to avoid winter injury. |

EXAMPLE 2

The following example describes the maintenance practices for a natural turfgrass athletic field, recreation area, or aesthetically pleasing sward which was either housed indoors or outdoors and subjected to reduced light conditions as described previously (less than ⅓ full sunlight, or 650 μmol/m$^2$/s of PAR, or less than 20 mol/day PAR over at least an eight hour photoperiod but greater than 6 mol/day) for at least three (3) hours per day. Lack of sufficient light was the major obstacle to maintaining a proper turfgrass sward. Secondary complications, stemming from the lack of sufficient natural light for turfgrass growth and environmental controls, included intense disease pressure, weak plants with thin cuticles and cell walls, high levels of free surface moisture for extended periods of time, and decreased turfgrass metabolism and insufficient growth to recover from disease and worn areas.

The management practices described below were for an established field, at least two months old. Ambient light levels were constantly monitored, and supplemented to maintain 10 mol/day PAR, with a 1:1 ratio of blue to red light, and a minimum of green light (500 to 560 nm range), over a 12 hour photoperiod. The turfgrass stand was composed of a single type or mix of cool season grasses (e.g. *Poa pratensis* L. and /or *Lolium perenne* L.) typically grown in a temperate, continental climate (e.g. the state of Michigan in the north midwest region of the United States). The turfgrass stand was rooted (roots at least 1–2 inches depth) into the soil, and was sufficiently dense that weed species comprise less than ⅟₁₀₀ of 1 percent of the total area. Insects were not a problem; thus, control of weeds and insects was not addressed. Proper maintenance (mowing, fertilization, watering, etc.) of the turfgrass sward prevented weeds and insects from becoming a problem. The soil was a mixture of sand:peat:soil in an 8:1:1 ratio (v/v) with characteristics as previously described.

The area under the reduced light conditions had temperature and humidity control, particularly the ability to heat the area and keep soil and air temperatures in an optimum range (50°–75° F.). Ideally air conditioning is available, but the ability to control humidity (40–60% RH) through air movement is essential.

All assumptions and management practices described were based on conducting 21 experiments, during a 23 month period, in conditions herein described. The knowledge gained includes that gained from the construction, installation, and management of a full scale portable indoor/outdoor natural grass soccer field at the Pontiac Silverdome as in Example 1. The descriptions are also based on knowledge accumulated by the authors during the management of a 320 ft$^2$ natural turfgrass sward permanently housed inside a facsimile of the Pontiac Silverdome stadium on the campus of Michigan State University. The fiberglass fabric (Sheerfill; from ChemFab Inc., Merrimack, N.H.) covering the Silverdome facsimile transmits approximately 10% of natural sunlight and is of the same material as that which covers the Pontiac Silverdome and other covered or shaded turfgrass fields around the world.

Description of management practices for the assumed parameters

Lighting

Minimum light levels were held to at least 6 mol/day PAR for turfgrass subjected to little or no traffic. Light levels were held to at least 10 mol/day PAR for turf subjected to intense traffic (e.g. sporting events such as soccer, baseball, or football). These light levels were supplied to the turf over at least an eight (8) hour photoperiod and may include ambient light.

The light levels stated above were supplied by forcing or allowing the transmission of natural sunlight to all areas of the turfgrass sward. Alternatively, the ambient light levels were supplemented to meet the above requirements with the use of artificial lighting systems as previously described.

Plant growth regulators

The use of Type II PGRs to suppress gibberellin biosynthesis in turfgrass under reduced light conditions (as defined previously) was critical for maintaining a high quality turf. Due to the logarithmic efficacy of the PGRs on the turfgrass plants, multiple applications of PGR were necessary to maintain a steady state of turfgrass quality throughout the year. Application of the PGRs were timed appropriately so as not to result in phytotoxicity. Application rates were as described on the PAR labels for multiple applications (e.g. 0.5 lb ai/A flurprimidol). Application of additional PGR can result in phytotoxicity if sufficient residual PGR exists in the turfgrass plant(s). Metabolism of the residual PGR in the turfgrass depended on the generally uncontrollable interaction of a number of factors, such as light, heat, grass types, fertility levels within the turfgrass plant, and growth stage of the turfgrass plants. While some control can be exerted on all factors listed except for the growth stage of the turfgrass plants, it was impossible to control the interaction of all factors due to the inherent genetic and microclimatic differences within the turfgrass sward.

Fertility

The nitrogen requirement for this turf system was 1.0 lb N/1000 ft$^2$/month applied as urea at 0.5 lb N/10000 ft$^2$ on a biweekly basis. The potassium requirement was 1.0 lb K$_2$O/1000 ft$^2$/month applied as muriate of potash at 0.5 lb K$_2$O/1000 ft$_2$ on a biweekly basis. The phosphorous requirement was 0.3 lb P$_2$O$_5$/1000 ft$^2$/month applied on a monthly basis. The iron requirement was 0.2 lbs Fe/1000 ft$^2$/month applied on a biweekly basis at 0.1 lb Fe/1000 ft$^2$. The magnesium requirement was 0.2 lbs Mg/1000 ft$^2$/month applied on a biweekly basis at 0.1 lb Mg/1000 ft$^2$.

The following Table 2 outlines the typical maintenance program during a 12 month period for a turfgrass system, utilized for athletic practices and matches, maintained under reduced light.

TABLE 2

BREAKDOWN OF IMPORTANT MANAGEMENT TECHNIQUES FOR AN INDOOR TURFGRASS SYSTEM INTENDED FOR SPORTS TURF USAGE

Date of Activity

| Month | Light | PGR | Irrigate | Dry (air movement) | Mow | Groom | Roll* | Fungicide | Sporting activity | Overseed/ Sod |
|---|---|---|---|---|---|---|---|---|---|---|
| | | | | Day of Month | | | | | | |
| Sept. | Daily | 1 | 2 | 3–8 | Daily | Daily | | 3; Sterol inhibitor + mancozeb | Yes | |
| Oct. | Daily | | | | Daily | Daily | | 1; Iprodione | Yes | |
| Nov. | Daily | 1 | 2 | 3–8 | Daily | Daily | | 3; mancozeb | Yes | |
| Dec. | Daily | | | | Daily | Daily | | 1; thiophanate methyl | Yes | |
| Jan. | Daily | 15 | 16 | 17–22 | Daily | Daily | | 14; Iprodione | Yes | |
| Feb. | Daily | | | | Daily | Daily | | 1; mancozeb | Yes | |
| Mar. | Daily | | 2 | 3–8 | Daily | Daily | | 3; Iprodione | Yes | |
| Apr. | Daily | | a | | Daily | Daily | | b | Yes | As needed |
| May | Daily | 15 | 16 | 17–22 | Daily | Daily | | b | No | As needed |
| June | Daily | | | | Daily | Daily | | 1; mancozeb | No | |
| July | Daily | 15 | 16 | 17–22 | Daily | Daily | | 1; Iprodione | No | |
| Aug. | Daily | | | | Daily | Daily | | 1; mancozeb | No | |

*Rolling can be done as needed to eliminate bumps and depressions on the surface. It is most effective when applied to moist soil (e.g. days following irrigation).
$^a$Irrigation is to be supplied as needed to reseeded or resodded areas. Pregerminated seed is to be used when overseeding to minimize the wetting periods needed as wetting periods favor disease development.
$^b$Fungicides to control Pythium blight need to be spot-applied when overseeding with *L. perenne* (e.g. metalaxyl or propamocarb). Additional fungicide applications to control diseases due to the extra wetting periods may be needed. Also, beginning at this time of year, applications may be needed to control dollarspot as well as leafspot/melting out, rusts, and pink snow mold.
$^c$Apply at label rates for specific disease control.

It is intended that the foregoing description be only illustrative of the present invention and that the present invention be limited only by the hereinafter appended claims.

We claim:

1. A method for providing an indoor activity field with natural turfgrass under reduced light conditions which limit growth of the turfgrass which comprises:

periodically applying a Type II plant growth regulator (PGR) to the turfgrass which inhibits gibberellin biosynthesis, while maintaining low surface moisture by providing air movement of 3 to 22 mph over the turfgrass, and using disease control chemicals and fertilizing chemicals, including nitrogen, potassium, phosphorus, iron, and magnesium, with a radiation level of at least about 1 mol/day PAR (Photosynthetically Active Radiation) on the indoor activity field.

2. The method of claim 1 wherein the air movement is by means of a fan or blower.

3. The method of claim 1 wherein the PGR is selected from the group consisting of paclobutrazol, flurprimidol, and trinexapac.

4. The method of claim 1 wherein the PGR is flurprimidol.

5. The method of claim 4 wherein the PGR is applied at a rate of between about 0.5 to 1.0 lb ai/acre at an intervals of not less than six weeks.

6. The method of claim 1 wherein the nitrogen is between about 1.0–2.0 lbs N/1000 ft$^2$/month, wherein the potassium is between 1.0–2.0 pounds as $K_2O$ per month, wherein the phosphorus is 0.15–0.30 lb $P_2O_5$ per 1000 ft$^2$/month, wherein the iron is 0.1 to 0.4 lbs Fe/1000 ft$^2$/month and the magnesium is 0.1 to 0.4 Mg/1000 ft$^2$/month.

7. A method for providing an indoor activity field with natural turfgrass under reduced light conditions which limit growth of the turfgrass which comprises:

(a) providing the turfgrass in multiple assembled containers each liftable and moveable with a fork type lift truck and containing a soil which is substantially sand so that the soil resists compaction, in an outdoor setting which is exposed to ambient light adjacent to the activity field and with cutting and watering as needed;

(b) applying a Type II plant growth regulator (PGR) which inhibits gibberellin biosynthesis to the turfgrass just prior to moving the containers with the forklift truck to the indoor activity field;

(c) fitting the modular containers together on a flat base defining the indoor activity field;

(d) using the indoor activity field for an activity for a period of time between about 10 and 60 days, while maintaining low surface moisture, providing air movement of 3 to 22 mph over the turfgrass, and using disease control chemicals and fertilizing chemicals including nitrogen, potassium, phosphorus, iron and magnesium and with a radiation level of at least 1 mol/day PAR (Photosynthetically Active Radiation) on the indoor activity field; and (e) removing the modular containers to the outdoor setting for a period of time to rejuvenate the turfgrass for subsequent use on the indoor activity field.

8. The method of claim 7 wherein the air movement is by means of a fan or blower.

9. The method of claim 7 wherein the PGR is selected from the group consisting of paclobutrazol, flurprimidol and trinexapac.

10. The method of claim 7 wherein the PGR is flurprimidol.

11. The method of claim 10 wherein the PGR is applied at a rate of between about 0.5 to 1.0 lb ai/acre at an intervals of not less than six weeks.

12. The method of claim 7 wherein the nitrogen is between about 1.0–2.0 lbs N/1000 ft$^2$/month, wherein the potassium is between 1.0–2.0 pounds as $K_2O$ per month, wherein the phosphorus is 0.15–0.30 lb $P_2O_5$ per 1000 ft$^2$/month, wherein the iron is 0.1 to 0.4 lbs Fe/1000 ft$^2$/month and the magnesium is 0.1 to 0.4 Mg/1000 ft$^2$/month.

* * * * *